United States Patent [19]

Stoy

[11] Patent Number: 4,731,079
[45] Date of Patent: Mar. 15, 1988

[54] INTRAOCULAR LENSES

[75] Inventor: Vladimir Stoy, Princeton, N.J.

[73] Assignee: Kingston Technologies, Inc., Dayton, N.J.

[21] Appl. No.: 935,224

[22] Filed: Nov. 26, 1986

[51] Int. Cl.$^4$ .......................... A61F 2/16; A45C 13/10
[52] U.S. Cl. ..................................... 623/6; 128/303 R; 206/5.1
[58] Field of Search ............................ 623/6; 206/5.1; 128/303 R

[56] References Cited

U.S. PATENT DOCUMENTS

| | | | |
|---|---|---|---|
| 3,589,363 | 6/1971 | Banko | 128/303 R X |
| 3,996,935 | 12/1980 | Banko | 128/305 X |
| 4,002,169 | 1/1977 | Cupler, II | 128/305 X |
| 4,063,557 | 12/1977 | Birdsall et al. | 351/160 R |
| 4,078,564 | 3/1978 | Spina et al. | 128/303 R X |
| 4,113,088 | 9/1978 | Binkhorst | 623/6 X |
| 4,191,176 | 3/1980 | Spina et al. | 128/1 R |
| 4,206,518 | 6/1980 | Jardon et al. | 623/6 |
| 4,253,199 | 3/1981 | Banko | 623/6 |
| 4,254,509 | 3/1981 | Tennant | 623/6 |
| 4,373,218 | 2/1983 | Schachar | 623/6 |
| 4,466,705 | 8/1984 | Michelson | 623/6 X |
| 4,508,216 | 4/1985 | Kelman | 206/5.1 |
| 4,537,943 | 8/1985 | Talcott | 528/15 |
| 4,542,542 | 9/1985 | Wright | 623/6 |
| 4,556,998 | 12/1985 | Siepser | 623/6 |
| 4,573,998 | 3/1986 | Mazzocco | 623/6 |
| 4,615,703 | 10/1986 | Callahan et al. | 623/6 |
| 4,638,056 | 1/1987 | Callahan et al. | 623/6 X |

OTHER PUBLICATIONS

AA—Cataract (Apr. 1984), pp. 18–19, Phema.

Primary Examiner—Ronald L. Frinks
Attorney, Agent, or Firm—Alan M. Sack; Richard C. Woodbridge

[57] ABSTRACT

There is provided a novel intraocular lens and mode of insertion therefore. The lens is of conventional shape and dimensions but is made of polymeric material having a softening point in the range of body temperature. The lens, prior to insertion is dimensionally reduced to enable introduction thru a small incision by compression or by axial extension. The deformed lens is frozen in this configuration by cooling the lens below its softening temperature. The cooled, deformed lens is then inserted into the eye. The action of body heat, optionally supplemented by various non-harmful methods, permits the lens to regain its original configuration within the eye.

24 Claims, 23 Drawing Figures

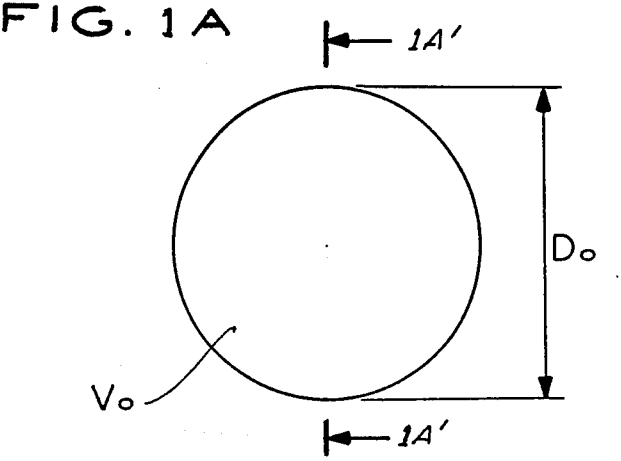
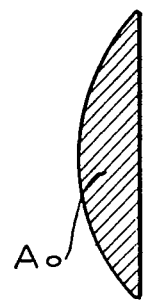
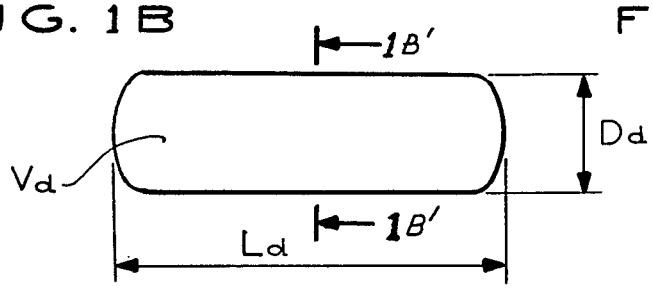
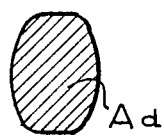
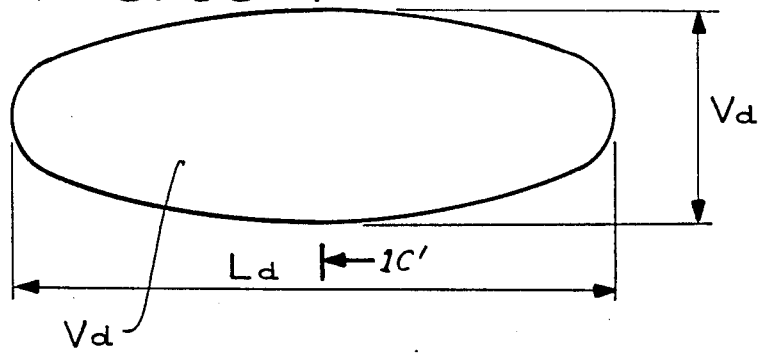
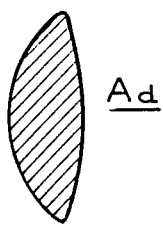
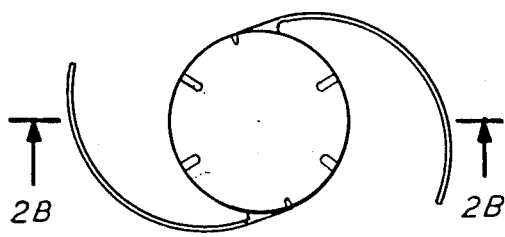
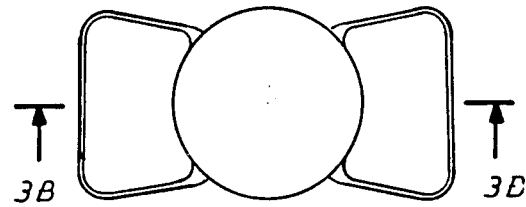
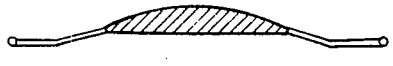

INTRAOCULAR LENSES

BACKGROUND OF THE INVENTION

An intraocular lens (IOL) is an optical device which is implanted into the anterior chamber (i.e., anterior to iris) or posterior chamber of the eye to replace the natural crystalline lens damaged by cataract, injury, etc.

IOLs are usually made mostly of clear arcylic resin (polymethylmethacrylate or PMMA), a rigid, glassy polymer. Since the PMMA IOL is about 6 mm in diameter in the narrowest axial cross-section (i.e., the plane including optical axis), the incision has to be appropriately large.

New surgical techniques and instruments allow for removal of the cloudy natural crystalline lens (i.e., cataract) through a much smaller incision than 6 mm (typically 2-3 mm). The major advantages of the small incision are lesser trauma, lower loss of intraocular pressure and aqueous humor during the surgery, easier healing and lesser risk of astigmation due to scar contraction.

In addition, these techniques (e.g., facoemulsification) permit only partial removal of the lens. Only the opacified geleous substance need be removed, while the lens capsule, or at least its posterior part, is left intact. The lens capsule is then utilized to keep the IOL in the proper location or, it can be even refilled by a suitable medium to restore its optical function.

DESCRIPTION OF THE RELATED ART

The techniques and instruments for such procedures are described, for instance, in U.S. Pat. Nos. 3,589,363; 4,063,557; 3,996,935; 4,078,564; and 4,191,176. The vacant capsule can be filled either with liquid (U.S. Pat. Nos. 3,996,935 and 4,002,169; or U.S.S.R. Pat. No. 570,363), or with a silicone elastomer (U.S. Pat. Nos. 4,537,943 and 4,542,542) to renew its optical function.

The advantages of the facoemulsification cannot be fully utilized if the IOL cannot be inserted through a small incision. For this reason, a number of IOL designs and surgical technqiues were proposed and tested. Some of the IOL designs are made from flexible materials such as silicone rubber or covalently cross-linked hydrogels.

For instance, U.S. Pat. No. 4,253,199 (A. Banko) describes a deformable IOL prepared from soft, elastomeric materials, such as hydrogels. U.S. Pat. No. 4,206,518 (F. Jardon, et al.) as well as U.S. Pat. No. 1,198,131 (Birdsall, et al.) describe IOLs made of a medical grade silicone elastomer.

U.S. Pat. No. 4,254,509 (J.L. Tennant) describes an IOL made at least partly from elastomeric materials such as hydrogels. According to CATARACT (April, 1984, pp. 18-19) PHEMA hydrogel lenses which are partially hydrated before insertion, have been used as IOLs since 1976.

Although the above flexible lenses were not designed specifically for facoemulsification procedure, the concept of facilitating insertion by using a flexible IOL is indicated in several sources.

U.S. Pat. No. 4,573,998 (T.R. Mazzoco) describes a method for the placement of an IOL through a small insertion by using an IOL made from an elastic material and deforming the IOL while it is being inserted. Usually the IOL is deformed by folding it into a "taco" shape.

The disadvantage of this approach is that folding the IOL requires considerable deformation in the center of the optical zone which, in turn, can cause permanent deformation and various other defects, such as crease marks and the like.

The use of softer materials which could be easily deformed without causing a permanent deformation causes another problem. Very soft materials have little incentive to entirely unfold to their original shape in the highly viscous intraocular environment. In addition, the lens folding and its manipulation in the folded state is highly sensitive to the individual surgeon's skill. Even more importantly, simple folding is not suitable for maximum decrease of lens cross-section during insertion. Adjacent surfaces of the lens cannot be entirely brought together (because this would cause maximum deformation in the optical zone) and an instrument has to be used to keep the lens folded during the insertion so that the IOL penetrates through the incision. The instrument together with the lens, effectively increases the lens cross-section.

The more convenient modes of deformation are not readily achievable in practice for an elastomeric lens, since the instrument needed for deformation is also the insertion instrument. For this reason, various other approaches have been suggested which do not depend on simple folding or rolling.

For instance, U.S. Pat. No. 4,373,218 (R.A. Schacher) describes an inflatable IOL which can be inserted in a folded and deflated state through a small incision. Another approach is the insertion of a deswollen hydrogel lens which swells in place by imbibing water from surrounding aqueous humor. The disadvantage here is that a substantial water content is needed to achieve the needed dimensional change. If the swelling is isotropic, the IOL has to swell 8 times by volume to increase its diameter from about 3 mm in the dry state, the size of the incision, to 6 mm, the usual size of an IOL. Therefore, the lens has to contain about 85% water (by volume) in its final state. However, most hydrogels are structurally weak at such a high water content. More importantly, the refractive index of such hydrogel is low (about 1.36 in the above example), so that the lens surface has to be more curved and hence, the lens has to be thick in the center to achieve the required refractive power. For this basic reason, the deswelling itself is not enough to permit insertion through a small incision. It is necessary to reshape the IOL in its non-swollen state so that the swelling simultaneously changes the volume and shape of the IOL.

One method proposed to achieve this aim is to design the IOL as a capsule composed of strong semipermeable membranes with a highly swellable gel or a water-soluble polymer entrapped in the capsule.

According to U.S. Pat. No. 4,466,705 (P.E. Michaelson), the dry lens can be folded for insertion into the eye, and then unfolded and blown into biconvex shape by osmotic pressure in the capsule. The potential disadvantage of this solution is the fact that the concentration of the polymer inside the capsule has to be rather high (at least 40-50%) to achieve the required refractive index (about 1.40). Accordingly, the pressure inside the capsule is permanently high. Although it is claimed that the membranes are sufficiently strong to withstand the resulting pressure of several tens of p.s.i., the presence of the pressurized capsule presents a certain long-term hazard. In addition, the optical properties which are dependent on the swelling are rather difficult to control.

Another method is the use of a hydrogel which is rigid enough in the non-swollen state to keep a shape suitable for insertion, but flexible and swellable enough to return to its inherent shape once it is inserted and fully swollen. Such a lens and method of surgery is described in U.S. Pat. No. 4,556,998 (S.B. Siepser). One obvious advantage of this approach is that the final swelling does not need to be high because the decrease of cross-section is achieved by a simultaneous change of shape and increase in size. For instance, the lens can be dried in a longitudinally extended shape so that its lateral cross-section is substantially decreased. The cross-section can be also changed into other than lenticular shapes (e.g., circular, rectangular, elliptical, etc.) which are more suitable for insertion.

An additional advantage of this IOL in comparison with the deformation of an elastic IOL is that a rigid lens can be readily manipulated during the insertion and an instrument (such as forceps) is not needed in order to maintain the deformed shape of the lens. Accordingly, the instrument does not need to be inserted into the incision simultaneously with the lens.

The concept of IOL swelling in situ has several inherent disadvantages. The most serious one is that the underswollen hydrogel is not in thermodynamic equilibrium with vitreous humor or tissues in its vicinity. As the hydrogels imbibe water from the environment, they concentrate proteins and other vitreous components on the interface. This can, in turn, cause protein denaturation, irreversible sorption and related biocompatibility problems. If such underswollen hydrogel contacts tissue, it adheres to the tissue and tends to destroy cells it contacts by breaking their membranes or simply tearing them off.

This cannot be readily prevented merely by the use of viscoelastic lubricating agents such as hyaluronic acid solutions. Such a solution can trigger the swelling and relaxation prematurely, a matter which is difficult to control in practice. Furthermore, if the viscoelastic solution becomes more concentrated as it loses the water to the hydrogel, its lubricating properties decrease as well. Another disadvantage of swelling in situ is that the full swelling takes considerable time. Thus, its result as to vision, fixation, etc. cannot be checked and eventually corrected during surgery.

Still another disadvantage is that the IOL cannot be sterilized by heat since the heating above a certain temperature would trigger relaxation and shape changes which have the same negative effects as premature swelling. Autoclaving is even less desirable than dry-heat sterilization, since the steam would cause both swelling and relaxation. Other methods of sterilization, such as ethylene oxide or gamma-irradiation, would pose their own specific problems.

SUMMARY OF THE INVENTION

There is provided an intraocular lens arrangement comprising a non-toxic, biocompatible, hydrolytically and enzymatically stable, photodegradation resistant, polymeric optical zone portion. The polymeric material of the intraocular lens arrangement, when in osmotic equilibrium with aqueous humor, has the following characteristics:

Softening temperature $T_s$ between about 0° C. and about 42° C., preferably between about +10 and +30° C.

Damaging temperature $T_d$ above 42° C. A refractive index greater than 1.39. The polymeric material can be heated in its temperature range of elastic deformation $T_e$, above $T_s$ but below $T_d$, without damage.

The polymeric optical zone portion of the lens will return to its original dimension at a temperature $T_e$ which is above $T_s$ and below $T_d$ under the following conditions:

Initial deformation of the optical zone by reducing a given dimension by at least 20%, using pressure or transverse stretching, at a temperature $T_s$ or above, but less than $T_d$. Cooling the optical zone to at least 5° C. to 10° C. below $T_d$ to maintain deformation. Reheating the polymeric optical zone of the lens $T_e$, allowing it to return to its original dimensions prior to its initial deformation.

$T_s$ is the softening temperature at which the polymer may be readily deformed but at or above which it will readily return to its previous shape upon release of the deforming force. $T_d$ is the temperature above which the polymer will be permanently deformed and damaged. The designation of $T_s$ and $T_d$ as definite temperatures is inexact for most polymers. The effect takes place within about ±3° C. of a designated temperature.

At temperatures above $T_s$ and in the absence of outside deforming forces, the intraocular lens exists in a shape designed as the Optical Configuration (OC) in which it has at least one convex surface which is symmetrical along the optical axis. Preferably, the lens has a refractive power from about +10 to about +35 Diopters in an aqueous immersion, and has an optical zone diameter from about 5 to about 9 mm. In the absence of outside deforming forces, the Optical Configuration of the IOL is maintained even if it is cooled below $T_s$.

The IOL according to this invention, can be reshaped into the Insertion Configuration (IC) which has a shape different from that of the Optical Configuration and which is selected to optimize insertion into the eye regardless of its optical properties.

Preferably, the shape of the IC is such that any cross-section lateral to a selected direction has an area smaller than about 4 mm$^2$, and more preferably smaller than 2.5 mm$^2$. Also, any linear dimension of such cross-section is smaller than 3.5 mm and preferably smaller than 2.5 mm.

The IOLs according to this invention can be temporarily reshaped into the IC by applying a suitable stress at a temperature higher than $T_s$, preferably between about 40° C. and about 100° C.

Once reshaped into IC, the IOL is cooled down to a temperature below $T_s$, preferably to a temperature between about −5° C. and about $(T_s-5)$° C. The IOL in the IC at such a temperature is essentially undeformable, rigid and capable of maintaining its shape during its insertion into the eye, without the need to apply outside forces or causes a deformation of any kind.

After the IOL is inserted and properly placed in the eye, it returns into its inherent Optical Configuration after its temperature reaches body temperature which is higher than $T_s$.

Preferably, the polymeric material can be plastizable by water or isotonic aqueous solutions containing biocompatible solutes. The polymeric material is a copolymer derived from at least two co-monomers, wherein at least one of the co-monomers is hydrophilic and the other may be hydrophobic.

It is often desirable that the copolymer additionally comprises a cross-linking agent. It may also comprise an outer hydrogel layer capable of maintaining a water content greater than 90% by weight when inserted in the eye.

The invention also includes a sterile package comprising a lens as previously described, packaged with a clamping or stretching means. The clamping or stretching means is used for reshaping the lens into the IC at a temperature above $T_s$ and below $T_d$. The sterile package also includes an autoclavable encapsulating means surrounding the lens and the clamping or stretching means.

In one embodiment of the package, the lens is located within the clamping or stretching means, in its inherent optical configuration (i.e., unshaped). Alternatively, the lens in the package has been reshaped into the IC and it is maintained in this configuration by the clamping or stretching means.

The invention also includes a method of introducing and implanting an artificial intraocular lens through an incision in the eye for replacement of a surgically removed natural crystalline lens, comprising the steps of:
(a) providing an intraocular lens as previously described;
(b) increasing the temperature of said lens to or above $T_s$ but below $T_d$ of the polymer;
(c) reshaping the lens at this temperature into Insertion Configuration as defined above;
(d) cooling the lens to a temperature between about $-5°$ C., and $5°$ to $10°$ C. less than $T_s$, while maintaining said IC;
(e) inserting said lens in the IC at a temperature lower than $T_s$, essentially in a rigid and non-elastic state, through an incision in the eye at a location posterior or anterior with respect to the iris; and,
(f) allowing the lens to be warmed to the temperature of the eye, above $T_s$, so that the lens will resume its Optical Configuration to provide safer, less traumatic and more convenient surgical procedure.

The dimensional reduction of the lens may be achieved at a temperature at or above $T_s$, but less than $T_d$, either by extension along a longitudinal axis of the lens or compression transverse to a longitudinal axis or a combination of both.

BRIEF DESCRIPTION OF THE DRAWINGS

FIG. 1A is a plan view of the optical zone of the lens of the present invention in its undeformed optical configuration.

FIG. 1A' is a cross-sectional view of the lens illustrated in FIG. 1A taken through line 1A'—1A' in the direction of the arrows.

FIG. 1B is a plan view of the optical zone of the lens illustrated in FIG. 1A in the Insertion Configuration which is achieved by compression of the lens.

FIG. 1B' is a cross-sectional view of the lens illustrated in FIG. 1B taken through line 1B'—1B' in the direction of the arrows.

FIG. 1C is a plan view of the optical zone of the lens illustrated in FIG. 1A in the Insertion Configuration which is achieved by extension of the lens.

FIG. 1C' is a cross-sectional view of the lens illustrated in FIG. 1C taken through line 1C'—1C' in the direction of the arrows.

L, A, V and D, are the length (i.e., maximum dimensions), the cross-sectional area, the volume and the dimension (transverse to L), respectively, of the optical zone of the lens. The dimensions of the optical zone of the lens in the Optical Configuration are symbolized by an "$_o$", and by a "$_d$" in the Optical Configuration; where $D_o > D_d$, $A_o > A_d$, $L_d > D_o$ and $V_o = V_d$.

FIGS. 2 through 8 (A and B) are plan and cross-sectional views, respectively, of several examples of the lens/haptic combinations usable in this invention.

Figure 4A:
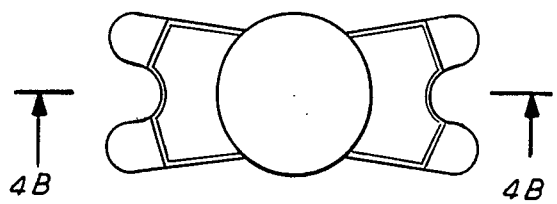
Figure 4B:
Figure 5B:
Figure 5A:
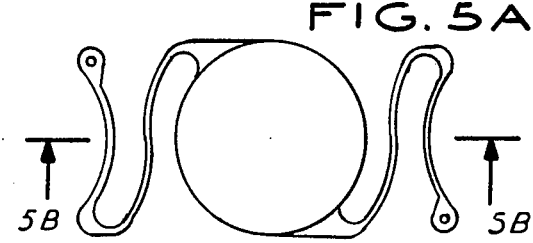
Figure 6B:
Figure 7B:
Figure 6A:
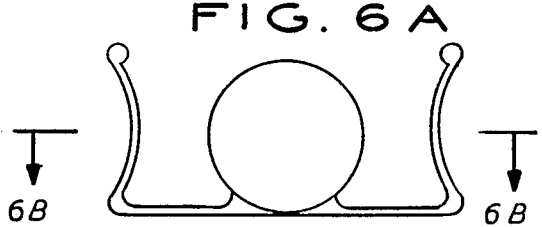
Figure 7A:
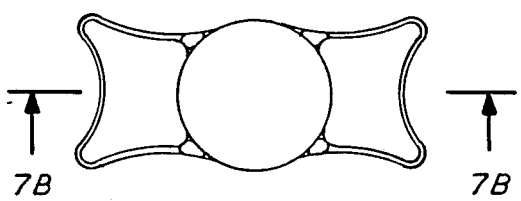
Figure 8B:
Figure 8B:
Figure 8A:
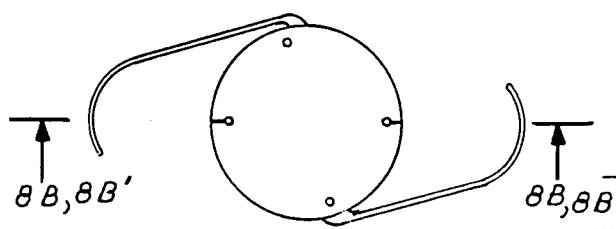

FIG. 8B' is an alternate cross-sectional view of the lens/haptic combination illustrated in FIG. 8A.

Figure 9:
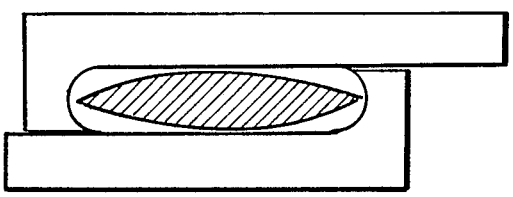

FIG. 9 is a schematic cross-sectional view of a lens in a clamping means in the Optical Configuration.

Figure 10:
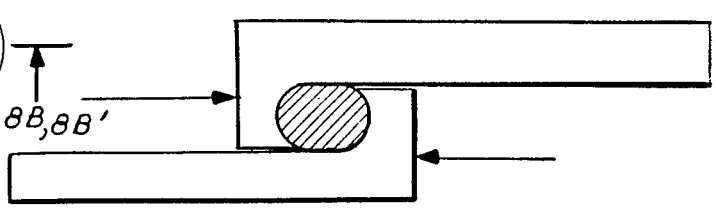

FIG. 10 is the schematic cross-sectional view of the lens in the clamping means illustrated in FIG. 9 shown in the Insertion Configuration, compressed in the direction of the arrows.

DESCRIPTION OF THE PREFERRED EMBODIMENTS

The intraocular lens is inserted into an incision in the eye. The intraocular lens is in the Insertion Configuration (IC), preferably at a temperature lower than $T_s$ (about $5°$ C. and more preferably by more than $10°$ C.) at which the polymer is essentially rigid and non-elastic and the IC is maintained without an application of an outside force.

The IC is the shape in which the IOL's cross-section including its optical axis, is preferably, smaller than about 4 mm$^2$, and more preferably less than 2.5 mm$^2$; and in which no linear cross-sectional dimension lateral to the insertion axis is larger than about 3.5 mm, preferably less than 3 mm. The IC is imparted onto the IOL by outside forces, preferably by compression in an appropriately shaped tool, at a temperature of about $T_s$, preferably at least $5°$ C. and more preferably at least $15°$ C. above $T_s$ but below $T_d$. The IC is maintained by cooling the IOL to a temperature below $T_s$, preferably to at least $5°$ C., more preferably to about $10°$ C. below $T_s$.

After the IOL is inserted in the eye and properly placed, it returns to its inherent Optical Configuration (OC) as its temperature reaches body temperature (higher than $T_s$). The body temperature is, as a rule, between about 36 and $37°$ C. Body temperature can be temporarily increased by several degrees using various means, such as infrared heating, hot compresses or microwave irradiation. For the purpose of this invention, the "body temperature" is the highest temperaure to which the intraocular temperature can be safely raised, even for a short period of time ($42°$–$43°$ C.).

The softening temperature ($T_s$) is the lowest temperature at which the lens can be substantially deformed without breaking or fracturing, and return completely to its original shape when the outside pressure is released. Below $T_s$, the material is essentially rigid and cannot return completely to its original shape by mens of its internal forces. $T_s$ may correspond to glass-transition temperature $T_g$ which has a well known and well defined meaning. In some cases however, $T_s$ and $T_g$ are not identical, e.g., in cases of two-phase polymerc systems, or the dual character of interaction between polymer chains. In such a case, $T_s$ is best defined as the lowest temperature at or above which there is no permanent residual deformation after removing a previously applied external stress. The recovery from deformed to inherent shape is not and need not be immediate. The complete recovery of shape can be achieved after a period as long as several hours without substantial problems. Although it is preferred that full recovery of shape take place in less than about 30 minutes, and more preferably in less than about 5 minutes.

The recovery to the original shape is much slower below $T_s$ than above $T_s$, so that it is not complete even after a very long time period. The relaxation processes slows down considerably with decreasing temperature so that at several degrees below $T_s$, the polymer is rigid and does not return into its inherent shape at any appreciable rate or extent. Due to the physical nature of the relaxation process, the transition between practically rigid and practically flexible state, extends over a certain range of temperatures rather than at a single sharply defined temperature. Accordingly, $T_s$ is defined arbitrarily with respect to the practical goals of this invention.

In addition to having a $T_s$ in the above range, the material of this invention is required to have good shape memory due to the presence of a covalent or strong physical network, and cannot suffer permanent deformation at temperatures higher than at least 37° C. The polymer can be reversibly deformed at a temperature higher than $T_s$ up to a ceiling temperature $T_d$ above which it is thermally damaged. $T_d$ is preferably higher than about 125° C. In addition to the above requirements, the material must be highly transparent to visible light and have a refractive index higher than about 1.39 and preferably higher than about 1.45.

In addition, the material of this invention has to be biocompatible, non-toxic, hydrolytically and enzymatically stable, and resistant to photodegradation.

There are a considerable number of polymers and copolymers which meet the basic requirements of this invention, i.e., (1) $T_s$ between 0° and 42° C., preferably between 15 and 30° C.;
(2) Optical clarity;
(3) Refractive index over 1.39, preferably over 1.45;
(4) Good shape memory and no permanent deformation above 36° C. and preferably above 30° C.;
(5) Sufficient hydrolytic and enzymatic stability;
(6) Photostability; and
(7) Non-toxicity and biocompatibility.

The polymers with such properties can be found among polyurethanes, polyureas, polyethers, polyesters, and the like.

Another class of polymers where suitable properties can be found are co-polysiloxanes, particularly those with a high content of aromatic and/or highly polar substituents.

The preferred class of polymers are the polyacrylates and polymethacrylates, particularly those containing an appropriate combination of lower and higher alkyl acrylates to place $T_s$ in the required range. Particularly useful is the group of copolymers containing C2 and C8 alkyl acrylates and methacrylates in combination with co-monomers with higher $T_g$, such as methylmethacrylate, styrene, methyl-styrene, vinylpyrridine and similar copolymers.

Still another useful class of copolymers are those containing N-alkyl and N,N-dialkyl acrylamides and methacrylamides.

It is well known that the $T_s$ of copolymers can be adjusted by combining co-monomers, one having $T_s$ lower and the other higher than the target $T_s$. Therefore, it is relatively easy for those skilled in the art to synthesize a large array of copolymers with $T_s$ in the range useful for the present invention.

The temperature of softening $T_s$ can be decreased by the use of plasticizers. The concentration of plasticizer needed to decrease the $T_s$ of a polymer below 37° C. depends on both the polymer and the plasticizer, but it is usually below about 40% by weight and more often below about 20% by weight of the polymer/plasticizer combination. The plasticizers useful in the present invention must have a very low toxicity. There are a number of plasticizers known to those skilled in the art which are suitable for medical applications. The preferred plasticizer is water or an isotonic aqueous solution (saline, Ringer solution, plasma and the like).

There are a number of known polymers which do not substantially swell in water (as do hydrogels) but whose $T_g$ or $T_s$ is decreased by absorbed water. The specific polymers of this class which are suitable for the present invention are those whose $T_s$ decreases in the presence of equilibrium concentration of water below 42° C. and preferably below 30° C.

The numerous polymers capable of plastification by water are those having both hydrophilic and hydrophobic moieties in their structures. Examples of such polymers are derivatives of cellulose or certain copolymers and terpolymers containing hydrophilic and hydrophobic monomers. A particularly preferred co-polymer is a combination of at least two co-monomers composed of the following: A first monomer component which when polymerized forms a hydrophobic polymer with a $T_s$ higher than 37° C.; and, a second monomer component which when polymerized forms a hydrophilic polymer or hydrogel. Because water itself depressed $T_g$ of the hydrophilic moiety, the resulting copolymer can have $T_s$ in the preferred range if plasticized with water, regardless of the $T_s$ of such copolymer in a dry state. Furthermore, it is advantageous if the copolymer has high $T_s$ in a dry state, while its $T_s$ is below 37° C. when swollen to equilibrium. Such copolymers can be readily lathed and polished into optically perfect surfaces in the dry (xerogel) state and then plasticized with water and reshaped into the IC prior to insertion.

Water-plasticized polymers or hydrogels have a number of advantages in comparison with hydrophobic polymers. For instance, they have a certain level of permeability for water and water-soluble compounds. Accordingly, they present less of a barrier to diffusion transport (whichis often important for biocompatibility) than hydrophobic polymers. The same permeability facilities cleaning and extraction of low molecular weight compounds such as residual monomers and the like, so that long-term leaching of toxic residuals is a lesser problem than in the case of hydrophobic polymers.

The hydrophilic surface has a lesser tendency to absorb certain proteins, such as albumin, than a hydrophobic surface. One accepted explanation of this phenomenon is a lower interfacial free enthalphy at equilibrium between the hydrophilic surface and the surrounding aqueous liquid, as compared with a hydrophobic interface and the surrounding aqueous liquid. The interfacial free enthalpy is the cause and driving force of sorption at the thermodynamic level.

Hydrophilic surfaces are usually poor substrates for the attachment and spreading of cells, particularly if the surfaces are highly hydrated, smooth and homogenous. The hydrophilic surface is also less likely to cause protein denaturation upon its sorption. Strong and irreversible protein sorption of hydrophobic implants may be the reason for auto-immune reactions, consecutive protein sorption, cell adhesion and spreading, and promotion of adverse reactions of the implant.

The water-plasticized copolymers which are particularly useful in the present invention are copolymers of hydrophobic monomers such as styrene, methyl styrene, methylmethacrylate, benzylmethacrylate, cyclohexylmethacrylate, viylcarbazole, vinylnaphthalene, 2-vinylthiopentene, naphthylmethacrylate, 2,6-dichchlorostyrene, o-chlorostyrene, pentachlorophenyl methacrylate, p-methoxystyrene, diphenylmethylmethacrylate, N-(2-phenylethyl)-methacrylate, N-butylemthacrylamide, methacrylonitrile, acrylonitrile, vinylpyrridine, or pentabromophenyl-methacrylate, which are co-polymerized with hydrophilic monomers such as acrylamide, N-methylacrylamide, acrylic acid, methacrylic acid, vinylpryyolidone, maleic acid, methacrylamide, glyceryl acrylate or methacrylate, mono-, di- or tri-ethyleneglycol monoacrylate or methyacrylate, 2-aminoethylacrylate or methacrylate vinyl alcohol, or vinyl sulfonic acids or salts.

The good shape memory required by the present invention can be best achieved by covalent cross-linking. The cross-linking of many polymer systems is well known in the art and is not the object of this invention. For instance, the cross-linking can be achieved by chain transfer during polymerization; by copolymerization with polyfunctional co-monomers; by post- cross-linking of polymers via reactions of side groups with various polyfunctional compounds such as aldehydes, epoxides, diisocyanates and the like.

The cross-linking agents are particularly important in the above-mentioned water-plasticized copolymers formed by at least one hydrophobic and at least one hydrophilic co-monomer. The cross-linking, in this case, is preferably caused by the presence of a monomer with two more polymerizable double bonds, such as glycol diacrylate or dimethyacrylate, where "glycol" means a molecule with 1 to 6 ($-OCH_2CH_2-$) units; divinylbenzene; methylene-bis-acrylamide; diallylphthalate; phenylallylmethacrylate; N-allylmethacrylamide; allylmethacrylate; vinylmetharylate and N-vinylmethacrylamide, or glycerol di- or tri-acrylate or methacrylate. The cross-linking density has to be appropriate to the particular polymer system. If the cross-linking density is too high, then the polymer may be too rigid or brittle to be deformed with $T_g$. If the cross-linking density is too low, the shape memory may be too low or too slow for achievement of recovery to be useful in an IOL. The appropriate cross-linking density can be readily found by those skilled in the art for a specific polymer system. As a rule, one link per 100 to 500 monomer units is sufficient, although it can be as low a 1 link per 1000 units or as high as 1 link per 20 units for a particular polymer.

A particularly preferred material for use in IOLs according to the present invention is a terpolymer consisting of a hydrophobic monomer, a hydrophilic monomer and a minor concentration, less than 5% and more preferably less than 2%, of a monomer with at least two polymerizable double bonds. Particularly preferred are terpolymers where both hydrophilic and hydrophobic monomers form homopolymers with a $T_g$ higher than about 50° C., more preferably higher than about 80° C. Another material requirement is absence of permanent deformation above about 36° C. This is another reason for the preference in the cross-linked polymers. Additionally preferred are polymers which are amorphous, without a substantial amount of crystalline polymer phase. The absence of the crystalline phase can be detected, for instance, from an X-ray diffraction pattern of the polymer.

Optical clarity in the visible spectral range is a natural requirement related to the polymer homogeneity. A suitable polymer may have heterogeneities such as polymer domains with different compositions and refractive indecies. However, as long as these heterogeneities are small enough compared with wavelength of visible light, for example, smaller than about 400 nm, their presence can be beneficial because of their intensive light scattering in the UV region. The size of the domains can be kept in the aforementioned range even with incompatible moieties, e.g., hydrophilic and hydrophobic monomer units or sequences, if the minor component is present in an amount lower than about 40 mol %. In addition, polymer cross-linking can diminish the size of the domains in certain polymer systems.

The beneficial effects of high surface hydration on protein sorption, general biocompability and surface lubricity have been discussed above. It is preferred that the lens of the present invention have a surface layer with a water content of over 50%, more preferably over about 90%. The surface properties of the lens are thereby improved without diminishing its shape retention capability or shape memory of the basic polymer at a temperature below $T_s$. This is in contrast to the in situ swelling IOLs which have to be inserted in the dehydrated state. The highly hydrophilic layer, particularly the dehydrated layer, tends to adhere strongly to tissues. Accordingly, it should be avoided in in situ swelling IOLs. Because the IOL, whether made from a hydrophobic or hydrophilic polymer, is already in an equilibrium state during insertion, it can be readily equipped with a permanent or a temporary layer which has a high water content. The temporary layer may be, for instance, a coating of an aqueous solution of hyaluronic acid salts or a similarly useful viscoelastic solution.

The permanent hydrogel layer can be made by surface hydrophilization by some of the methods which are well known in the art for various polymers. The surface hydrophilization can be based on oxidation, hydrolysis, transesterification and the like. As long as the swelling gradient thus formed is regular, the optical properties of the IOL do not deteriorate and the optical quality is rather insensitive to the thickness of the hydrophilic layer. The swelling gradient also causes the formation of a refractive index gradient, which, in turn, decreases the reflection of incoming light.

The permanent hydrogel layer can also be made by encapsulation of the IOL in a highly swollen hydrogel. As long as the surface water content is higher than about 90%, and preferably higher than 95%, the refractive index of such a layer is sufficiently close to that of vitreous humor so that the outside surface geometry or quality becomes optically insignificant. These highly hydrated hydrogel polymers are soft and their presence does not affect the IOL material's $T_s$. Accordingly, the highly hydrated hydrogel polymers do not adversely affect the retention of the Insertion Configuration by the lens or its return to the Optical Configuration.

The preferred hydrogels in the outside layer, whether formed by chemical modification, encapsulation or by another method, are those containing negatively charged groups, such as carboxyls, sulfo-groups, sulphate or phosphate groups. The hydrogels in the outer layer of the lens can be either cross-linked chemically or physically and may or may not contain a crystalline polymer phase. Since the hydrogel layer does not significantly affect the IOL's mechanical characteristics, the limitations and preferences discussed in connection with the basic IOL material do not entirely apply for the hydrogel layer (with the exception of nontoxicity, biocompatibility, optical clarity and the like). As mentioned above, the hydrogel layer thickness is not important per se, but practical considerations limit the thickness of the hydrogel layer to between about 1 to 100 microns, and usually between about 5 and 50 microns.

The hydrogel layer can have various thicknesses in various parts of the IOL. For instance, the layer can be very thin in the central optical zone and the thickest in the peripheral parts or haptics. For instance, the outside shape of the hydrogel layer may be planar, with refraction taking place between the hydrogel layer and the actual encapsulated IOL.

An important component of each IOL is the so-called haptic, or the part designed for IOL attachment to the internal eye structures, e.g., capsule or ciliary body. The haptics can have various designs and configurations and they can be made from the same material as the optical part, or from a different material, e.g., polypropylene threads. Encapsulation of the haptics in an inert hydrogel can solve numerous biocompability problems often related to haptics.

The IOLs of the present invention can use various designs of haptics. It is preferred however that haptics are more readily deformable than the optical parts of the IOL. This way, the in vivo capsule contractions do not deform the optical zone of the lens. In addition, it is preferred that the haptics can be deformed more readily in the plane perpendicular to the optical axis than in other directions. In such configurations, the capsule contractions do not push the lens toward the iris, which is very sensitive to contact with foreign materials. One example of haptics design with these preferred properties are the incomplete loops or S-shaped protrusions of the IOL polymer, integral with the optical part, encapsulated in a much softer hydrogel with a high water content. Some examples of IOL designs for both anterior and posterior implantation, suitable for the present invention, are shown in FIGS. 2 to 8.

The IOL, according to the present invention, can be reshaped to the shape appropriate for insertion ("Insertion Configuration") at any time during or after manufacture, but prior to insertion. For instance, the IOL can be brought into the "Insertion Configuration" as part of the manufacturing process. In this case, the IOL would have to be constantly kept at low temperatures, including during the steps of sterilization, shipment and storage. Therefore, it is advantageous to construct the package in such a way that the "Insertion Configuration" is maintained in the package, regardless of temperature. This can be done by keeping the IOL in a clamp or in a cavity in the package having a shape which matches the shape of the "Insertion Configuration". In this way, the package can be autoclaved in the "Insertion Configuration" and stored or shipped at a temperature higher than $T_s$.

Another approach is to package, autoclave and ship the IOL in its "Optical Configuration" and transform the IOL into the "Insertion Configuration" after opening the sterile package just prior to the surgery. Because the transfer from the "Optical" to the "Insertion Configuration" is very fast and simple, this transformation can be done by a nurse or a surgeon without a problem. The procedure includes several simple steps:

(1) placing the undeformed IOL into a shaping tool;
(2) heating the tool and device above $T_s$ (usually higher than 37° C., preferably about 50° C.) in an appropriate medium, such as warm sterile saline;
(3) compressing the IOL into its Insertion Configuration shape;
(4) cooling the IOL and the tool below $T_s$;
(5) removing the rigid IOL in Insertion Configuration from the tool;
(6) applying a viscoelastic agent, if needed, and inserting the lens in Insertion Configuration through the incision by means of forceps, a tubular applicator, or the like.

In place of Step 3, being a compressing step, the IOL may be stretched along its longitudinal axis (i.e., direction of insertion). A combination of compression and stretching may also be used.

The shaping tool can be a simple sterile, disposable device, or a more complicated sterilizable device. The cooling and heating of the IOL can be done by immersing the tool with the IOL into an appropriate sterile medium (preferably isotonic saline), or it can be caused by internal heating and/or cooling elements of the shaping tool. The shaping tool can also be designed to facilitate or to perform the insertion of the IOL into the eye.

Some simple shaping tools are described in the Examples.

The novel method of implanation of the IOL, according to the present invention, is convenient for the patient and for the surgeon. Both the size of the incision and the time necessary for implantation are diminished in comparison with the alternative methods.

The intraocular lens, according to the present invention, is reshaped at a temperature above $T_s$ into a shape suitable for its insertion, cooled below $T_s$ to fix the Insertion Configuration, and maintained below $T_s$ until it is inserted into the eye. Once implanted, the lens is heated to the body temperature which is above $T_s$, which causes the lens to return to its Optical Configuration. The return to the Optical Configuration is faster than the return caused by swelling, so that the position of the lens can be checked and altered during surgery. More importantly, the lens is always in osmotic equilibrium with vitreous humor so that any transient, nevertheless potentially harmful conditions of protein sorption and tissue adhesion are avoided.

The lens can also be used in connection with viscoelastic agents, and provided with an outside hydrophilic layer. Thus, the lens can be inserted into the eye with the hydrogel layer in a fully swollen, lubritious state. This way, all disadvantages of the IOL swelling in situ, discusse in *The Description of The Related Art* are avoided. Moreover, the lens can be shaped for insertion immediately prior to surgery by a very fast and simple procedure. Accordingly, the insertion shape can be customized for the particular surgical technique, in a particular situation and according to the preference of a particular surgeon. Custom deformation of the IOL cannot be done with a lens deformed in a non-swollen state.

The shape for insertion can be selected so that the minimum cross-section is achieved without bending or folding the optical zone. The most preferred shape is achieved by compression against the edges as indicated in FIG. 1A, 1A' (Optical Configuration and cross-section) and 1B, 1B' (Insertion Configuration and cross-section).

Another preferred reshaping method is the extension of the lens in the direction lateral to the smallest final cross-section as indicated in FIGS. 1A and 1C (Optical and Insertion Configuration, respectively).

These two methods can be advantageously combined so that the lens is simultaneously reshaped by extension in the direction of haptics and by compression by an appropriately shaped tool against the lens edges perpendicular to the extension. The type of reshaping described above is far superior to folding or bending because the deformation is evenly distributed through the lens. Therefore, a substantial change of overall shape is achieved without any large local deformation.

In addition, when assuming its Optical Configuration, there is no part of the lens which has to travel over long distances through a highly viscous medium; which is the case with IOLs that are inserted by folding and assume their Optical Configuration by unfolding.

Therefore, the present invention solves not only the problem of insertion through a small incision, but more importantly, the problem of a fast and safe return of the IOL into its Optical Configuration.

One substantial advantage of the present invention over insertion of a deformed elastic lens, described in the prior art, is that the IOL is inserted in IC while it is rigid and nonelastic. Therefore, it maintains its shape which is optimum for insertion without any mechanical means or tools. The shaping tool and the insertion tool may be different instruments, each optimized for a single purpose. The rigid and non-elastic IOL in the IC increases convenience to the surgeon as well as decreases the risk of accidental and sudden decompression. Accidental and sudden decompression may occur when elastic lens is forcefully compressed during insertion, resulting in loss of control of the lens and possible injury to the patient.

The lens, according to the present invention, is suitable for insertion not only by means of forceps or other holding instruments, but also by means of various tubular applicators, injectors, and the like. Use of these applicators makes the IOL insertion a faster, more efficient and a less traumatic procedure.

EXAMPLE I 100 grams of n-butylmethacrylate (nBMA), free of inhibitor, were mixed with 1.1 grams of ethylenglycoldimethacrylate (EGDM) and 0.05 grams of azo-bis-isobutyronitrile (ABIN). The mixture was purged with nitrogen and poured into polypropylene molds which were made from disposable plastic syringes.

The molds filled with a polymerization mixture, were heated in a water bath to 65° C. for five hours, and then the temperature was increased to 90° C. for four hours to decompose the rest of the initiator and to complete the polymerization. The blocks of cross-linked Poly nBMA were then removed from the molds, cut into disks about 2 mm thick and 10 mm in diameter.

The disks were extracted in ethyl alcohol in a Soxhlet apparatus for several hours to remove unincorporated residues, dried in an oven at 80° C., and then dried under vacuum at 60° C. to a constant weight. Some of the clear disks of the cross-linked Poly nBMA were cooled in a water-ice mixture and lathed to form a biconvex IOL having a diameter of 6 mm. The lathing and polishing was readily done as long as the polymer was cooled below about 12 to 15° C. and held in a precooled chuck.

The refractive index of the polymer was 1.484, as measured by using an Abbe refractometer on a thin slice of the polymer.

The radius of curvature was 14.9 mm. The refractive power was determined to be +21 Diopters, as measured by a Vertexometer in a wet cell filled with saline. The edge thickness of the lens was 0.15 mm and its central thickness was 0.76 mm. The undeformed cross-section in an axial plane had an area of 3.35 square mm.

The lens was inserted into the cavity of a length of natural rubber tubing with an I.D. of 4 mm and a wall thickness of 3 mm. The tubing was then heated in a water bath to about 60° C., extended to about seven times its length, and cooled while extended in a water-ice mixture. The tubing was relaxed and the deformed IOL was readily removed. The lens had a roughly cylindrical shape with a length of about 6.5 mm, a diameter of about 1.6 mm and a cross-sectional area of about 2 mm². The lens was readily insertable through a facoemulsification incision (3.3×1.6 mm, and a cross-sectional area of about 4.2 mm²). Once heated to 37° C. in saline, the IOL recovered to its exact original shape, dimensions and optical parameters. The whole procedure was repeated several times without any observable deterioration of the lens quality.

Disks of IOL material with a diameter of 10 mm and a thickness of 2 mm were used to determine the $T_s$ of the polymer in the following way:

(1) A disk and a stainless steel pin (O.D.=1.5 mm) were heated in saline to about 50° to 60° C. for about 5 minutes;

(2) The disk was wrapped tightly around the pin, quenched in saline at a temperature of 0° C. for about 5 minutes;

(3) The pin was placed in the cooled saline horizontally, with folded side of the disk turned down, and the temperature of the saline was slowly increased (1° C. every 2 to 3 minutes);

(4) At a certain temperature, the disk partially unfolded and fell to the bottom of the container; this temperature was recorded as $T_s1$;

(5) At a slightly higher temperature, the disk returned to its original flat shape, with no observable residual deformation. This temperature was recorded as $T_s2$;

(6) The softening temperature was calculated as $T_s=(T_s1+T_s2)/2$.

In this particular Example, $T_s1$ was found to be 18.5° C. and $T_s2$ was 23° C., so that $T_s=20.75°$ C.

EXAMPLE II 85 grams of benzyl Acrylate, 15 grams of styrene and 0.35 grams of tetraethyleneglycol-bis-metharylate were polymerized under nitrogen by means of 0.075 grams of benzoylperoxide. Temperature was kept at 65° C. for the first 19 hours, and then the temperature was raised to 110° C. for 4 hours.

The polymer disks were again used to determine $T_s$ as described in Example I. The $T_s$ was 25.5° C. and the refractive index was 1.570.

The copolymer was lathed into the shape of a biconvex lens having a diameter of 6 mm, a radius of curvature of 15.67 mm and edge thickness of 0.15 mm. The lens had a refractive power in saline immersion of +31.5 Diopters. Its central thickness is 0.73 mm, and its area of cross-section in the axial plane is 3.22 mm².

The lens was then inserted in a tube made from a roll of stainless steel, 0.5 mm in thickness. The roll and the lens were immersed in nearly boiling water for several seconds, and the roll was tightened until its I.D. was less than about 1.6 mm. Then the roll containing the deformed lens was immersed in a jar of saline at a temperature of about 10° C. for several seconds.

The roll was slightly unwound to loosen the deformed lens, which was readily removed. The lens in the deformed state was about 6.6 mm long. The lens had a nearly cylindrical cross-sectional diameter of about 1.6 mm; and a cross-sectional area of less than 2 mm². The deformed lens was readily insertable through a facoemulsification incision by means of forceps or another suitable instrument.

Introduction of the lens into the eye may also be accomplished by means of a tubular instrument, such as a canula or a syringe needle. Also the deformation tool, i.e., the metal sheet roll, could be used to insert the lens through the incision.

After insertion, the lens was heated to at least 36° C., the reshaped lens completely recovered its original shape, dimensions and optical parameters, i.e., its Optical Configuration.

EXAMPLE III

To demonstrate the difference between the lens of the present invention, and a lens according to the current state of the art, a biconvex lens was made from medical grade silicon rubber (refractive index 1.42). Its radius of curvature was 5.67 mm, its diameter was 6.0 mm, its edge thickness was 0.15 mm, and its central thickness was 1.87 mm. Its area of cross-section in the axial plane was 7.9 mm², nearly twice the area of the facoemulsification incision.

The silicone rubber lens was placed into the instrument described in Example II, which was tightened with considerable force until its diameter was less than about 2.3 mm, so that it barely fitted into the incision, the cross-sectional area of the deformed lens was about 4.1 mm². An attempt was made to push the lens out of the instrument with a pin. Although the lens was lubricated, the lens could not be pushed until the roll was unwound to an I.D. of about 2.4 to 2.5 mm. As the lens exited the instrument, it was damaged as it expanded over the edge. When it was more than 50% out of the instrument, the lens popped out fast in an uncontrollable manner.

In another experiment, the lens was folded into a taco-like shape using forceps, and an attempt was made to insert the lens through a simulated incision with an elliptical hole measuring 3.3×1.6 mm. Insertion was utterly impossible. A comparison with Example II shows that the handling and the use of the IOL according to the present invention is safer and more convenient than the handling and use of optically similar silicone IOLs.

EXAMPLE IV 35 grams of methylmethacrylate was mixed with 65 grams of 2-hydroxyethacrylate containing 0.85 wt. % of ethylene-glycol dimethacrylate. 0.05 grams of azo-bis-isobutyronitrile were dissolved in the mixture, which was then purged briefly with nitrogen. The solution was drawn into polyproplylene syringes, enclosed and heated in water, containing about 0.25% sodium bisulfide, to 70° C. for 12 hours. The solution in the syringes polymerized without bubbles or vacuoles since the plunger compensated for contractions in the volume of the solution.

The hard plastic cylinders thus formed were readily removed from the molds i.e., syringes, heated in an oven for 12 hours to 105° C. at atmospheric pressure and then for another 12 hours at 0.3 Torr.

Thereafter, the cylinders were slowly cooled to ambient temperature. The polymer at this point was hard, and had a softening temperature of about 100° C. It was readily lathed and polished into the shape of biconvex IOL with integral haptics.

The finished lens was then placed in an isotonic saline solution for 24 hours at ambient temperature. From the lens' weight increase it was found that its equilibrium water content was about 10% by weight. The final parameters of the lens were as follows: Diameter: 6.0 mm; radius of curvature: 14.02 mm; central thickness: 0.80 mm; edge thickness: 0.16 mm; undeformed area of cross-section: 3.5 mm²; and, refractive power in saline immersion: 20.75 Diopters. The refractive index of the polymer in equilibrium with saline with 1.475.

The lens was inserted into the opening of the deformation tool schematically depicted in FIG. 9. The lens and tool were then heated by brief immersion into sterile saline at a temperature of about 65° C.

The jaws of the tool were then closed as shown in FIG. 10, and the tool including the lens were quenched for several seconds in iced saline. The tool was then opened and the lens, in the deformed cylindrical shape, was readily removed.

The length of the deform lens' optical part measured about 6.5 mm, it had a diameter of about 1.6 mm and its cross-sectional area was about 2.1 mm². The lens in that state was rigid, readily handable and insertable through a small incision. Unlike a dry-deformed hydrogel lens, this lens could be covered with aqueous lubricants or viscoelastic agents, as long as they were precooled below the $T_s$ of the polymer, approximately 22 to 25° C. Once heated to 37° C., the lens returned into its original shape and geometry.

EXAMPLE V 80 grams of 2-hydroxyethylmethacrylate, with a dimethacrylate content of 0.35 wt. %, was copolymerized with 20 grams of methylmethacrylate as described in Example IV. The resulting copolymer was equally capable of being lathed and polished as the copolymer of Example IV with the higher NMA content.

The copolymer was in equilibrium was saline and plasticized with about 19 wt. % of saline. The copolymer, plasticized with saline had a $T_s$ at about 9 to 11° C. The lens could be deformed at ambient temperature and quenched in ice-cooled saline. The lens had to be inserted in the eye through the incision without substantial delay. Once it was beyond the critical, i.e., the narrowest, point of entry, the lens recovered its original shape within several seconds so that it could be manipulaed inside the eye as an ordinary, albeit, a soft IOL. The advantage of the fast shape recovery is that surgeon can check the position and fixation of the lens without undue delay.

EXAMPLE IV

Several terpolymers were prepared with one common compound, ethyleneglycoldimethacrylate (1% by wt). The other two monomer components were:
ethylmethacrylate (36%)—n-hexylmethacrylate (63%);
n-butylmethacrylate (94%)—methylmethacrylate (63%);
methylacrylate (89%)—styrene (10%);

methylacrylate (55%)—methylmethacrylate (11%);
n-butylacrylate (55%)—methykmetacrylate (44%);
cyclohexylacrylate (94%)—cyclohexylacrylate (5%);
methylacrylate (79%)—ethylmethacrylate (20%);
ethylacrylate (59%)—ethylmethacrylate (40%);
glycolmonomethacrylate (59%)—methylmethacrylate (40%).

All of these terpolymers were found to have a $T_s$, when immersed in water, at the useful working range of 15° C. to 30° C. In addition, all these terpolymers completely recovered their original shape at 36° C. after being deformed at temperatures below their $T_d$, i.e., they exhibited complete memory.

I claim:

1. In an intraocular lens which includes at least a non-toxic, biocompatible, hydrolytically and enzymatically stable, photodegradation resistant, polymeric optical zone portion,
   wherein the improvement comprises said polymeric optical zone portion having the following characteristics, when in osmotic equilibrium with body liquids:
   (a) softening temperature $T_s$ between about 0° C. and about 42° C.;
   (b) damaging temperature $T_d$ higher than 42° C.;
   (c) refractive index greater than 1.39; and
   (d) temperature range of elastic deformation Te, above $T_s$ but below $T_d$, and
   when said polymeric optical zone portion is heated to $T_e$ and one of its original dimensions is reduced by at least 20%,
   then cooled to at least 5° C. below $T_s$ and,
   upon reheating to $T_e$ said polymeric optical zone portion will return to its original dimensions existing prior to said first heating to $T_e$, dimensional reduction and cooling.

2. A lens in accordance with claim 1 wherein said polymeric material is plastizable by water or isotonic aqueous solution containing a biocompatible solute.

3. A lens in accordance with claim 1 wherein the polymer is a co-polymer derived from at least two co-monomers.

4. A lens in accordance with claim 3 additionally comprising a cross-linking agent.

5. A lens in accordance with claim 3 wherein at least one of the co-monomers is hydrophilic.

6. A lens in accordance with claim 3 wherein at least one of the co-monomers is hydrophobic.

7. A lens in accordance with claim 6 wherein at least one of the co-monomers is hydrophilic.

8. A lens in accordance with claim 2 comprising an outer hydrogel lens capable of maintaining a water content greater than 90% by weight when inserted in the eye.

9. A lens in accordance with claim 8 wherein the thickness of the hydrogel layer is between 1 and 100 microns after swelling.

10. A sterile package comprising: a lens of claim 1, a dimension reducing means capable of reducing the dimension of said lens by at least 20% of its prereduction dimension, in a predetermined direction, after heating to a temperature above $T_s$ and below $T_d$ and autoclavable encapsulating means surrounding said lens and said clamping means.

11. A package according to claim 10 wherein said lens is located within said clamping means.

12. A package according to claim 11 wherein said lens is in the Optical Configuration.

13. A package in accordance with claim 11 wherein said lens has been reduced by at least 20% of its prereduction dimension in a predetermined direction in the Optical Configuration and is maintained in said reduced state by said dimension reducing means.

14. A method of introducing and implanting an artificial intraocular lens for replacement of a surgically removed crystalline lens, through an incision in an eye, comprising the steps of:
   providing an intraocular lens of non-toxic, biocompatible, hydrolytically and enzymatically stable, photodegradation resistant, elastomeric, polymeric material having the following characteristics:
   (a) $T_s$ between about 0° C. and about 42° C.;
   (b) $T_d$ above 42° C.; and
   (c) refractive index greater than 1.39;
   said lens having an optical axis and an axis transverse thereto designated as the longitudinal axis where said longitudinal axis is substantially coaxial with the direction of insertion of said lens into said incision in said eye;
   heating said lens to a temperature above $T_s$ and below $T_d$;
   reducing at least one dimension of said lens, in a direction transverse to said longitudinal axis, to a dimension at least 20% less than the pre-reduction dimension in said direction;
   cooling said lens to a temperature above −5° C. which is at least 5° C. less than $T_s$ while maintaining the reduced dimension of the lens;
   inserting said lens into said incision in said eye; and
   permitting the lens to warm to a temperature below 42° C. and above $T_d$;
   whereby said lens will return to its original dimensions of full size and fixed focal length to provide a safer, more convenient surgical procedure and a more comfortable fit in the eye.

15. A method of claim 14, wherein the dimension reduction is provided by tension applied along the longitudinal axis.

16. A method of claim 14 wherein the dimension reduction is prvoided by compression transverse to the longitudinal axis.

17. A method in accordance with claim 14 wherein said polymeric material is plasticizable by water or an isotonic aqueous solution containing a biocompatible solute.

18. A method in accordance with claim 14 wherein the polymer is a co-polymer derived from at least two co-monomers.

19. A method in accordance with claim 18 additionally comprising a cross-linking agent.

20. A method in accordance with claim 18 wherein at least one of the co-monomers is hydrophilic.

21. A method in accordance with claim 18 wherein at least one of the co-monomers is hydrophobic.

22. A method in accordance with claim 21 wherein at least one of the co-monomers is hydrophilic.

23. A method in accordance with claim 14 comprising an outer hydrogel layer capable of maintaining a water content greater than 90% by weight when inserted in the eye.

24. A method in accordance with claim 23 wherein the thickness of the hydrogel layer is between 1 and 100 microns after swelling.

* * * * *